United States Patent [19]

Eppley et al.

[11] Patent Number: 4,988,358

[45] Date of Patent: Jan. 29, 1991

[54] METHOD FOR PROMOTING HARD TISSUE GROWTH AND REPAIR IN MAMMALS

[76] Inventors: Barry L. Eppley, 7702C Chaterly Ct., Indianapolis, Ind. 46214; Marilyn D. Krukowski, 24 Washington Terrace, St. Louis, Mo. 63112; Philip A. Osdoby, 134 Holly Garden Dr., Ballwin, Mo. 63021

[21] Appl. No.: 291,175

[22] Filed: Dec. 28, 1988

[51] Int. Cl.$^5$ .................................................. A61F 2/28
[52] U.S. Cl. ........................................... 623/16; 623/66
[58] Field of Search ................ 623/16, 66; 128/92 W, 128/92 YR; 424/95

[56] References Cited

U.S. PATENT DOCUMENTS 4,643,735  2/1987  Hayes et al. ................ 128/92 W X
4,687,820  8/1987  Hou et al. .......................... 525/54.1

FOREIGN PATENT DOCUMENTS 0171546  9/1984  Japan ..................................... 623/16

*Primary Examiner*—Alan W. Cannon
*Attorney, Agent, or Firm*—Robbins & Robbins

[57] ABSTRACT

A material with chemically induced surface charges is employed to foster formation of mammalian hard and soft connective tissues. The material may be in the form of beads such as ion exchange resins. Bead materials with a negative surface charge stimulate formation of hard tissue within long bones and foster bony repair of defects in parietal bones and in mandibular rami. Beads with positively charged surfaces engender formation of large quantities of soft dense connective tissue when implanted into defects in the cranium or when used as an onlay on the nasal bone surface. The use of such beads or other charged biodegradable materials and the use of other surface charged materials with different physical configurations provides significant improvement in hard and soft connective tissue repair, augmentation and replacement in medical fields such as orthopaedic and maxillofacial surgery.

9 Claims, No Drawings

METHOD FOR PROMOTING HARD TISSUE GROWTH AND REPAIR IN MAMMALS

BACKGROUND OF THE INVENTION

This invention concerns materials with chemically induced surface charges for use in augmentation, repair and replacement of both hard and soft mammalian connective tissues. The invention could have direct application to a variety of clinical problems encountered in a number of medical fields, e.g., orthopaedic surgery and maxillofacial surgery.

In the realm of bone surgery there are many osseous defects of diverse etiology, e.g., non-union fractures, bone loss consequent to trauma, malignancy, or infection-induced sequestration, and bone deficits or abnormalities as a result of malformation. Thus, the ability to stimulate formation of bone at specific sites within the skeleton is of considerable clinical importance and a wide array of materials to initiate bone repair and/or to restore or replace missing bone has been examined.

Three major approaches are available to the problem of bone replacement. One is a strictly conformational method whereby defective or missing bone is replaced by an implant (of metal, ceramic or other inorganic material) intended to mimic the form, and optimistically the function, of the missing bone. In the past, this approach has been unsuccessful due to rejection of the material and/or failure of integration of the implant with normal skeletal tissue. More recently, some ceramic materials (hydroxyapatite, tricalcium phosphate) have shown acceptable biocompatability with, and healing in, defect sites with evidence of a direct bond to bone at the interface. These materials, however, lack the mechanical properties of bone, and additionally, bone fails to grow into and become incorporated within the implant. Such materials, then lack the capacity to substitute for natural bone in bone reconstruction.

Alternatively, missing osseous tissue may be substituted for with a matrix which functions as a passive support or scaffold around and into which new bone growth can occur. The matrix attracts, or "turns on", cells that have already been committed to an osteogenic pathway, a process referred to as osteoconduction. Allogeneic bone grafts (banked cadaver bone) succeed exclusively by this mechanism. However, their failure rate, as evidenced by graft loss, sequestration, and delayed healing, is unacceptably high (15-30%). Even when such grafts are well accepted, their healing periods for consolidation and capacity for mechanical stress-bearing are of long duration when compared to autogeneic bone grafting. Further, the present concern about transmissible viral agents, coupled with unfulfilled clinical expectations, has led to limited use of allogeneic grafts at present.

The third approach to bone replacement, involving osteoinduction, occurs when a material or substance induces the ingrowth of new bone from the host's undifferentiated tissues, typically around a temporary matrix. Such material is termed osteoinductive and a number of compounds have been shown to have such a capacity and are enumerated in detail in U.S. Pat. No. 4,440,750 to Glowacki. At present, the most promising of these factors has been "bone morphogenic protein" (BMP) which was extracted from demineralized bone using urea or guanidine hydrochloride and re-precipitated according to the disclosures in U.S. Pat. Nos. 4,294,753 and 4,455,256 to Urist. In addition, U.S. Pat. Nos. 4,434,094 and 4,627,982 to Seyedin and Thomas, respectively, report a substance termed "osteogenic factor" which appears to be a bone generation-stimulating, bone-derived protein. While substances such as these stimulate osteogenesis, the difficulty in using such a protein, or proteins, is that they are normally present at very low concentrations and require large amounts of starting material to obtain sufficient quantities for a few experiments let alone as a routine reagent for bone repair. Until molecular technology identifies the gene or genes for such factors, and recombinant molecules are obtained, the practicality of this approach is of limited clinical value.

Collagen-based solutions, which polymerize after injection or placement (U.S. Pat. Nos. 4,424,208 to Wallace and 4,347,234 to Wahlig), have also been described in U.S. Pat. No. 3,949,073 to Daniels for hard tissue augmentation. In addition, Hollinger, in U.S. Pat. No. 4,578,384, describeds a proteolipid incorporated into a biodegradable polymeric matrix comprised of a 50-50 polyacetic acid (PLA) and polyglycolic acid (PGA) for the healing of osseous tissue. The use of collagen-based polymers, however, presents several problems. Collagen, although generally biocompatible, is not completely biodegradable or resorbable and often becomes surrounded, and not absorbed, by host tissues. As such, when placed in a bone bed, where rigidity is ultimately desired, it represents a potential source of long-term mechanical failure. Additionally, collagen, being an organic substance most commonly commercially derived from bovines, allows for the possibility of allergic and immune reactions.

Thus, many of the criteria for an acceptable material for bone repair remain unsatisfied with present methodology. A replacement compound that is immunologically acceptable, nontoxic, osteoconductive or osteoinductive, readily available, capable of being shaped or molded, and capable of being integrated with existing bone tissues continues to be sought.

As with bone or hard tissue, the promise of alloplastic biomaterials that are effective in promoting or enhancing soft connective tissue repair and/or augmentation has not been fully realized. Silicone (dimethylpolysiloxane), introduced in 1964, was initially widely used because of its purported lack of absorption. Extensive clinical experience has shown, however, that an unacceptable number of complications, including granulomatous inflammatory changes, migration of the implant material, and chronic erythema of the overlying skin occur and, as a result, this material has never received FDA approval. Collagen in the commercial form of Zyderm and Zyplast (manufactured by Collagen Corp., Palo Alto, Calif.), introduced in 1979, has met with more encouraging results. It has proved effective, without significant side effects, in the adjunctive management of the aging face as well as in the primary treatment of small cutaneous defects from acne, trauma, or prior surgery. However, it is not permanent and repeated treatments are usually necessary to maintain correction. Thus, it is of little use for stimulating connective tissue production and the laying down of new tissue. It is, rather, an inert dermal filler which is shortly resorbed. In addition, because the material is of bovine origin, allergic and immune reactions can occur and are not rare phenomena. Lastly, the use of collagen is presently limited to small deficiencies and has no proven efficacy in large defects (requiring more than 5 cc of material). As such, collagen represents an improved, but limited, material for soft tissue repair and augmentation.

More recently, with the introduction of Fibrel (manufactured by Serono Laboratories, Inc., Randolph, Mass.) in 1987, there was a new type of soft tissue material which could stimulate connective tissue production rather than inertly fill space. Fibrel is a commercial form of a combination of collagen, gelatin, and epsilon aminocaproic acid which, most likely, acts like a reservoir for growth factors which are in high concentrations in coagulum around the collagen base. Early studies suggest that volume maintenance is prolonged but permanency is still not achieved. Furthermore, the inherent risks of bovine collagen, as previously mentioned, remain.

Thus, improved methodologies and diferent biologic approaches continue to be warranted in the search for materials to effect both hard and soft connective tissue repair and augmentation.

SUMMARY OF THE INVENTION

A series of observations provide a background for the use of charged beads for their osteogenic potential. First, demineralized bone powder without its surface charge lacks osteoinductive potential. Second, electric fields are helpful is fostering new bone formation. Third, some tested materials, e.g., hydroxyapatite and titanium, are effective in stimulating bone growth when presented in bead form. In the instant invention, it has been demonstrated that biodegradable beads with chemically induced surface charges promote not only bone or hard connective tissue formation, but soft connective tissue formation as well. The result appears to be dependent upon the charge in each respective application as well as on the recipient site.

The beads of the instant invention are not so important for their particular composition as they are for their physical qualities with regard to chemically charged surfaces created by functional groups. The beads of the instant invention generally are biodegradable organic compounds routinely used as ion exchangers common in many biochemical applications.

Beads with a negative surface charge stimulate formation of hard connective tissue, e.g., bone, within long bones and foster bony repair of defects in parietal bones and in mandibular rami. Beads with positively charged surfaces engender formation of large quantities of dense soft connective tissue when implanted into defects in the cranium or when used as an onlay on the nasal bone surface.

The mechanism(s) by which the charged beads cause bone or soft connective tissue to be generated is at present unclear. It may be that the charged environment alters cell surface moieties so as to permit the expression of osteogenic or fibroblastic potential. Alternatively, it may be that because of their charged surfaces, specific factors bind to the beads and thus effect formation of new bone or fibrous connective tissue.

The ion exchangers, or beads, of the instant invention are readily available and could be linked to a variety of materials. Such materials could be inert where the ion exchanger could exert its effect independently; others could have bone inductive ability (e.g., demineralized bone) where the ion exchanger could augment or facilitate that ability.

Thus, this invention envisions organic, biodegradable substrates, with chemically-induced surface charges, in the form of beads or in different condifurations, being used as: (1) material to be implanted into bony and non-bony defects to facilitate and expedite repair; or (2) material of an onlay or inlay to promote augmentation of bone or connective tissue mass; or (3) as material to function as a carrier for growth promoting factors.

The above features are objects of this invention. Further objects will appear in the detailed description which follows and will be otherwise apparent to those skilled in the art.

DESCRIPTION OF THE INVENTION

The biodegradable beads in the instant invention are ideally those biodegradable carbohydrate compounds employed as ion exchangers, which are produced by attaching functional groups onto a dextran matrix. A typical ion exchanger bead envisioned in the instant invention is Sephadex, a cross-linked dextran manufactured by Pharmacia Fine Chemicals. These beads with varying positive or negative functional groups are of a spherical gel nature with rigidity and good flow properties. The Sephadex ion exchangers are insoluble in solvents. They are stable in water, salt solutions, organic solvents, alkaline and weakly acidic solutions. In strongly acidic solutions below pH 2 hydrolysis of glycoside linkages may occur. The particle size is in the 40 to 120 micron range (120–325 mesh). They are produced by attaching functional groups to glucose units in the dextran matrix by stable ether linkages. Ion exchangers based on Sephadex G-25, an uncharged dextran, are tightly cross-linked and have minimal swelling and great rigidity. Because Sephadex is bead formed, it is easy to pack and administer to the site.

Different functional groups may be substituted onto the ion exchanger resulting in different degrees of anionic and cationic exchange capability. For example, two functional groups that are substituted onto Sephadex are diethylaminoethyl (DEAE) and carboxymethyl (CM) which result in a weakly basic anion exchanger and weakly acidic cation exchanger, respectively. DEAE Sephadex charged beads, therefore, have a positive surface charge and CM beads have a negative surface charge. The Sepahdex beads are desirably moistened in a biologically compatible solution to create an easy to administer paste or slurry. Alternatively, Tyrode's solution, i.e., a standard balanced salt solution, is employed in the amount of 5 ml to 1 cc of UV-sterilized beads to provide a suspension which may be administered through a 22 gauge needle.

Exemplary of other chemically induced charged ion exchangers that are biodegradable are the Sepharose and Sephacel beads of Pharmacia Fine Chemicals. The Sepharose beads may be provided with the diethylaminoethyl (DEAE) and carboxymethyl (CM) functional groups while the Sephacel beads may be provided with the first named functional groups. The Sepharose beads are derived from agarose while the Sephacel beads are derived from cellulose.

PRELIMINARY FINDINGS

1. Charged Beads and Osteogenesis in Young Birds—A One Week Study (Krukowski, M. et al., J. Bone Min. Res. 2 (Suppl. 1): Abstr. #278, 1987); Krukowski, M. et al., J. Bone Min. Res. 3:165, 1988) Three types of charged beads (Sephadex: DEAE, positive surface charge; CM, negative surface charge; G-25, uncharged) were injected into femora of sixteen day-old chickens. Beads with a positive surface charge were found: after three days, surrounded by multinucleated giant cells; by four days, with patches of bead-associated new bone along with giant cells; and after one week, with few giant cells but now surrounded by large quantities of new intramedullay bone forming an extensive bead-bone lattice which at times almost obliterated the marrow cavity. No bead-generated new bone was seen with negatively charged or uncharged beads at one week.

2. Charged Beads and Bone Formation in Yound Birds—A One-Month Study

Chick femora have been examined (two birds with each bead type: positive surface charge, negative surface charge, or uncharged) one month after intraosseous injection.

The uncharged beads when found lodged near the wall of the bone were occasionally seen with small quantities of new intramedullay bone. In contrast, beads away from bone were found in patches of condensed marrow with no evidence of any cell reaction, similar to observations with these beads after one week.

In the case of positively charged beads (the bead type responsible for the impressive osteogenic response at one week), after one month, and after serially sectioning completely through all specimens, no evidence of intramedually bone could be found nor were any beads or bead fragments visible anywhere in any section. Since in all other injected bones, at all other time points, beads, in greater or lesser amounts, could be visualized within the marrow cavity, it seemed unlikely that, of all the treated birds, only two at one month after injection of the positively charged beads would represent unsuccessful injections. It was concluded that the observations with positively charged beads at one week were transitory and that after a period of one month the advantages were not present.

It is suggested that the postively charged beads invoke a remodeling phenomenon beginning with resorption (large numbers of giant cells) at three days, new bone and giant cells at four days, and evidence oinly of the formative phase at day seven. It was speculated as to: whether another resorptive phase would follow; whether the beads would remain intact; and whether the intramedullary bone would persist. The findings in birds at one month, coupled with the speculations, along with observations in rats (see below) where positively charged beads were enveloped by multinuucleated giant cells which appeared to be ingesting the beads, support a wave of resorption which degraded such beads and simultaneously resorbed the positively charged bead-associated intrameduallary bone.

In contrast, beads with negative surface charges, after one month, were found sequestered in limited areas of the marrow cavity. Each bead, individually, was seen surrounded by bone, and the resulting bead-bone mass was encapsulated by a solid bony perimeter.

3. Charged Beads and Intrafemoral Bone Formation in Rats—A One Month Study

The three differently charged bead types were injected intrafemorally into rats (two with each bead type) and examined one month later (Krukowski, M. et al., Trans. O.R.S. 13:49, 1988). With uncharged beads, a bead-tissue lattice occupied large portions of the marrow cavity. Giant cells were not evident, the beads appeared intact, and the tissue component was dense, soft connective tissue. With negatively charged (CM) beads, giant cells were lacking, the beads, like the uncharged ones, were intact, but were seen enveloped by large quantities of bone resulting in a bead-bone mass that practically filled the entire marrow space. The bead-associated bone was viable, well-vascularized, and rich in osteocytes.

In contrast, the positively charged beads, those responsible for the osteogenic response in birds at one week, were seen in rats, at one month, to be associated with multinucleated giant cells. Some of the beads had irregular contours and bead fragments were seen in the cytoplasm of some of the giant cells, suggesting the multinucleated cells were actively ingesting the beads. Such ongoing destruction of this bead type in rats, at one month, is in line with their absence in one-month bird specimens. Such destruction or biodegradation by multi-nucleated giant cells is akin to removal of unwanted foreign materials by foreign body giant cells.

Findings following intrafemoral injection of beads in birds and rats are summarized in Table I. What is apparent is the agreement in both at one month. For positively charged beads, the beads are either gone or in the process of being degraded. With negatively charged or uncharged beads, the beads persist intact and only with the negatively charged beads is there associated bone in both vertebrates.

TABLE I

| | GENERATION OF BONE AND/OR GIANT CELLS IN RESPONSE TO INTRAFEMORALLY INJECTED CHARGED BEADS | | | | |
|---|---|---|---|---|---|
| | DAY 3 BIRD | DAY 4 BIRD | ONE WEEK BIRD | ONE MONTH BIRD | RAT |
| DEAE Positively Charged | Beads, GCs | Beads, GCs, Bone | Beads, Bone | ** ** | GCs ingesting beads |
| CM Negatively Charged | Beads, GCs | Beads, GCs Bone | Beads, GCs | Beads, Bone | Beads Bone |
| G-25 Uncharged | Beads, GCs Bone | Beads, GCs | Beads | Beads | Beads, Connective Tissue |

*In first week, an osteogenic response to CM and G-25 beads was seen when beads were juxtaposed to the endosteum or lodged in the growing metaphysis. Bone was solely bead-associated where indicated elsewhere.
**Neither beads nor new bone was observed.

4. Charged Beads: New Bone or Soft Connective Tissue in the Mammalian Craniofacial Region In preliminary trials, cranial and mandibular defects were packed with positively charged, negatively charged, and uncharged beads. Contralateral defects were left unfilled. One month later, the animals were sacrificed and bones with defects and/or beads were photographed, fixed and processed for histology.

Grossly, beadless defects, and those with uncharged beads, showed limited bone growth at the perimeter but otherwise were occupied by non-mineralized connective tissue. Defects with positively charged beads also contained soft connective tissue but lacked any new peripheral bone. In contrast, defects with negatively charged beads achieved partial bony closure in the cranium and full closure in the mandible.

Microscopically, unfilled defects, or those packed with uncharged beads, contained relatively loose connective tissue with some evidence of peripheral new bone ingrowth. In contrast, defects with positively charged beads were filled with dense, highly cellular soft connective tissue and had sharply defined margins devoid of new bone suggesting the beads had an inhibitory effect on bone ingrowth but had a stimulatory effect on fibroblastic activity. In addition, numbers of giant cells were visible with these positively charged beads.

Histological examination of nasal bone onlays gave results simular to those with cranial defects. Only with negatively charged beads was there evidence of new bone formation and beads that had been put in contact with the nasal bone surface were found, at one month, enveloped by new bone resulting in a sizeable bead-bone layer above the original bone. Also, onlays of positively charged beads resulted, at one month, in an impressive composite layer of dense connective tissue and beads.

In summary, negatively charged beads stimulate bone or hard connective tissue formation when injected into marrow cavities of long bones or when used as an onlay on the nasal bone surface. Similarly, the negatively charged beads foster bony repair of defects in the cranium and in mandibular rami. In contrast, positively charged beads stimulate production of dense fibrous connective or soft tissue evident in cranial defects and prominent in nasal bone onlays.

There may be employed a flat sheet containing the beads or various materials in different physical forms, i.e., a mesh, coated with functional groups such as those coating the beads. Such material may be cut into appropriate shapes and sizes to overlay or fill defects to provide a significant clinical value for augmentation and repair of bone and fibrous connective tissues. In addition, such materials may also serve as a vehicle to introduce growth factors to such hard and soft tissue sites.

The functional groups providing the chemically induced positive or negative charges may be incorporated as a surface coating in alloplastic devices or materials to provide the hard or soft tissue growth formation capability. Such alloplastic devices and materials may be joint replacements, hip sockets and bone plate fixation material, for example, using biocompatible materials exemplified by metals, bioceramics and plastics. Such materials may be biocompatible artificial materials that replace or augment natural hard or soft connective tissue exemplified by titanium, vitallium (an alloy of titanium and stainless steel), hydroxy apatite and plastics such as methyl methacrylate and Proplast and Silastic.

Various changes and modifications may be made within this invention as will be apparent to those skilled in the art. Such changes and modifications are within the scope and teaching of this invention as defined in the claims appended hereto.

What is claimed is:

1. A method for promoting hard tissue growth and repair in sites of tissue defects in living mammals which comprises applying an effective quantity of material with a deliberately produced chemically induced effective surface charge to said sites, the tissue site being bone and the deficit being caused by at least one of trauma, non-union fracture, malignancy and malformation in said bone and said charge material being applied to said site and said material being an ion exchange material having a negative charge, said effective quantity being sufficient to promote said growth and repair.

2. The method of claim 1 in which the material is biodegradable.

3. The method of claim 1 in which said material is applied in the form of small discrete spherical beads.

4. The method of claim 1 in which a fabric, mesh or sheet, containing said charge material is fashioned into an appropriate shape and size, and said fabric, mesh or sheet is placed onto said site.

5. The method of claim 1 in which the material serves as a vehicle for the introduction of growth factors into hard tissue sites for correction of defects.

6. The method of claim 1 in which the material is an integral component of alloplastic materials that may be used for at least one of hard tissue joint fixation, stabilization, reconstruction, and replacement.

7. A method for promoting hard tissue growth annd repair in site of tissue defects in living mammals which comprises applying an effective quantity of material with a deliberately produced chemically induced effective surface charge to said sites, said effective quantity being sufficient to promote said growth and repair, said tissue site being bone and the deficit being caused by at least one of trauma, non-union fracture, malignancy and malformation in said bone and said charge material being applied to said site, said material having a negative charge and said material being applied in the form of small discrete spherical beads, said beads being a biodegradable ion exchange material and comprised of a dextran matrix having functional groups.

8. The method of claim 7 in which the functional groups comprise carboxy methyl.

9. A method for promotingg hard tissue growth and repair in sites of tissue defects in living mammals which comprises applying an effective quantity of material with a deliberately produced chemically induced affective surface charge to said sites, said effective quantity being sufficient to promote said growth and repair, said tissue site being bone and the deficit being caused by at least one of trauma, non-union fracture, malignancy and malformation in said bone and said charge material being applied to said site, said material having a negative charge and said material being applied in the form of small discrete spherical beads, said beads being an ion exchange material and comprised of a dextran matrix having functional groups.

* * * * *